(12) United States Patent
Hyun et al.

(10) Patent No.: US 9,211,105 B2
(45) Date of Patent: Dec. 15, 2015

(54) IMAGE INDICATOR PROVISION IN AN ULTRASOUND SYSTEM

(75) Inventors: Dong Gyu Hyun, Seoul (KR); Norio Shinozuka, Hiratsuka (JP)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 733 days.

(21) Appl. No.: 12/693,347

(22) Filed: Jan. 25, 2010

(65) Prior Publication Data
US 2010/0191114 A1 Jul. 29, 2010

(30) Foreign Application Priority Data
Jan. 28, 2009 (KR) ........................ 10-2009-0006570

(51) Int. Cl.
A61B 8/02 (2006.01)
A61B 8/00 (2006.01)

(52) U.S. Cl.
CPC ................ *A61B 8/00* (2013.01); *A61B 8/4254* (2013.01); *A61B 8/463* (2013.01); *A61B 8/465* (2013.01); *A61B 8/466* (2013.01); *A61B 8/467* (2013.01)

(58) Field of Classification Search
CPC .. A61B 8/4254; A61B 8/4245; A61B 8/4263; A61B 19/5244; A61B 5/065; A61B 2019/5251; A61B 2019/5272; A61B 2019/5276
USPC .................................................. 600/437–461
See application file for complete search history.

(56) References Cited

U.S. PATENT DOCUMENTS

| 5,211,167 | A | 5/1993 | Amenomori |
| 6,290,649 | B1 | 9/2001 | Miller et al. |
| 6,436,040 | B1 | 8/2002 | Collamore et al. |
| 6,500,118 | B1 | 12/2002 | Hashimoto |
| 6,517,491 | B1 | 2/2003 | Thiele et al. |
| 7,063,660 | B2 | 6/2006 | Chen et al. |
| RE40,153 | E | 3/2008 | Westerman et al. |

(Continued)

FOREIGN PATENT DOCUMENTS

| EP | 1 523 940 A1 | 4/2005 |
| JP | 57-130259 U | 8/1982 |

(Continued)

OTHER PUBLICATIONS

European Search Report for Application No. 10150925.5-1265 mailed May 25, 2010, 7 pages.

(Continued)

*Primary Examiner* — Elmer Chao
(74) *Attorney, Agent, or Firm* — McDermott Will & Emery LLP

(57) ABSTRACT

Embodiments of providing image indicators together with an ultrasound image are disclosed. A mapping table including a plurality of objects each associated with examination locations, each of the examination locations being associated with one or more image indicators. The image indicators include a target organ marker indicative of each object, a body axis marker indicative of an anatomical orientation of each object, and an ultrasound beam direction marker indicative of a transmission direction of the ultrasound beam. A processing unit accesses the storage unit to provide the image indicators corresponding to a target object and examination location selected in response to selection instructions inputted by a user. The processing unit further 3-dimensionally rotates the image indicators based on position information of an ultrasound probe.

21 Claims, 4 Drawing Sheets

(56) References Cited

U.S. PATENT DOCUMENTS

| | | | |
|---|---|---|---|
| 7,352,570 B2 | 4/2008 | Smith et al. | |
| 2003/0065265 A1 | 4/2003 | Jackson et al. | |
| 2003/0195421 A1* | 10/2003 | Demers et al. | 600/437 |
| 2005/0038337 A1* | 2/2005 | Edwards | 600/424 |
| 2005/0203417 A1 | 9/2005 | Okuno | |
| 2007/0106146 A1* | 5/2007 | Altmann et al. | 600/407 |
| 2007/0239009 A1* | 10/2007 | Kawashima et al. | 600/437 |
| 2007/0255137 A1* | 11/2007 | Sui et al. | 600/443 |
| 2009/0124906 A1* | 5/2009 | Caluser | 600/443 |

FOREIGN PATENT DOCUMENTS

| | | |
|---|---|---|
| JP | 60-066735 A | 4/1985 |
| JP | 60-72541 A | 4/1985 |
| JP | 5-015531 A | 1/1993 |
| JP | 5-111488 A | 5/1993 |
| JP | 06-022966 | 2/1994 |
| JP | 8-154934 A | 6/1996 |
| JP | 1996-154934 A | 6/1996 |
| JP | 10-137242 A | 5/1998 |
| JP | 11-047133 A | 2/1999 |
| JP | 2000-132664 A | 5/2000 |
| JP | 2001-017433 A | 1/2001 |
| JP | 2002-263101 A | 9/2002 |
| JP | 2003-180696 A | 7/2003 |
| JP | 2003-260056 A | 9/2003 |
| JP | 2004-113629 A | 4/2004 |
| JP | 2005-006710 A | 1/2005 |
| JP | 2005-040301 A | 2/2005 |
| JP | 2005-118142 A | 5/2005 |
| JP | 2006-149481 A | 6/2006 |
| JP | 2007-202829 A | 8/2007 |
| JP | 2007-301030 A | 11/2007 |
| JP | 2007-330764 A | 12/2007 |
| JP | 2008-272370 A | 11/2008 |
| JP | 2008-301969 A | 12/2008 |
| KR | 10-2008-0042334 | 5/2008 |
| KR | 10-2008-0124197 A | 6/2010 |
| WO | 2007/133296 A2 | 11/2007 |

OTHER PUBLICATIONS

Korean Office Action issued in Korean Patent Application No. KR 10-2009-0006570 dated Apr. 13, 2011.

European Office Action issued in European Patent Application No. 10150925.5 dated Jul. 5, 2012.

Japanese Office Action issued in Japanese Application No. 2010-015396 dated Feb. 25, 2014, w/English translation.

Japanese Office Action with English translation issued in Japanese Application No. 2010-015396 mailed Jul. 30, 2013.

US 8,282,555, 10/2012, Kakee et al. (withdrawn).

N. Shinozuka, et al., "Transvaginal sonographic orientation detection system using ceramic gyroscopes," Journal of Ultrasound in Medicine, Feb. 1, 1996, vol. 15, No. 2, pp. 107-113 (Abstract Only).

Decision on Appeals issued in corresponding Japanese Patent Application No. 2010-015396, mailed on Jul. 28, 2015; with English translation.

* cited by examiner

| TARGET OBJECT | EXAMINATION LOCATION | TARGET ORGAN MARKER | BODY AXIS MARKER | ULTRASOUND BEAM DIRECTION MARKER |
|---|---|---|---|---|
| HEART | PARASTERNAL VIEW |  |  |  |
| | APICAL VIEW | | |  |
| | SUBCOSTAL VIEW | | |  |
| | SUPRASTERNAL VIEW | | |  |
| UTERUS | VAGINA |  |  |  |
| ⋮ | ⋮ | ⋮ | ⋮ | ⋮ |

IMAGE INDICATOR PROVISION IN AN ULTRASOUND SYSTEM

CROSS-REFERENCE TO RELATED APPLICATIONS

The present application claims priority from Korean Patent Application No. 10-2009-0006570 filed on Jan. 28, 2009, the entire subject matter of which is incorporated herein by reference.

TECHNICAL FIELD

The present disclosure generally relates to an ultrasound system, and more particularly to an ultrasound system that can provide image indicators corresponding to a target object.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional diagnostic images of internal features of an object (e.g., human organs).

Generally, the ultrasound system provides a relatively narrow view angle. This is so that scanning is performed for multiple examination locations of a target object to form ultrasound images corresponding to the respective examination locations. The ultrasound images may be outputted by using an echo printer. The examination is then implemented through the outputted ultrasound images. However, it may be difficult to intuitively recognize which part is scanned or which ultrasound image corresponds to an up, down, left or right ultrasound image of the target object. Thus, the ultrasound images may be outputted together with image indicators (e.g., icons) indicative of corresponding examination parts. The image indicators may be also referred to as body markers. The image indicators may be overlaid on the ultrasound images as texts. For example, if a user selects a text button on a control panel provided by the ultrasound system, then a text input window may be activated on the ultrasound image. The user may manipulate a track ball mounted on the control panel to position a cursor on the text input window for text input. Inputting the text may be performed by using a keyboard, which is also mounted on the control panel. However, inputting the text in such fashion may take a long time and greatly inconvenience the user. Also, since the image indicators are directly selected by the user, the image indicators may be incorrectly set.

SUMMARY

Embodiments for providing image indicators in an ultrasound system are disclosed herein. In one embodiment, by way of non-limiting example, an ultrasound system comprises: a sensing unit configured to sense a 3-dimensional position and/or orientation of an ultrasound probe to form position information and/or orientation information; and a processing unit configured to rotate one or more image indicators corresponding to a target object and an examination location 3-dimensionally based on the position information and/or the orientation information of the ultrasound probe.

In one embodiment, there is provided a method of providing an image indicator in an ultrasound system including an ultrasound probe, comprising: a) sensing a position and/or an orientation of an ultrasound probe by using a sensing unit to form position information and/or orientation information; and b) 3-dimensionally rotating one or more image indicators corresponding to a target object and an examination location based on the position information and/or the orientation information.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
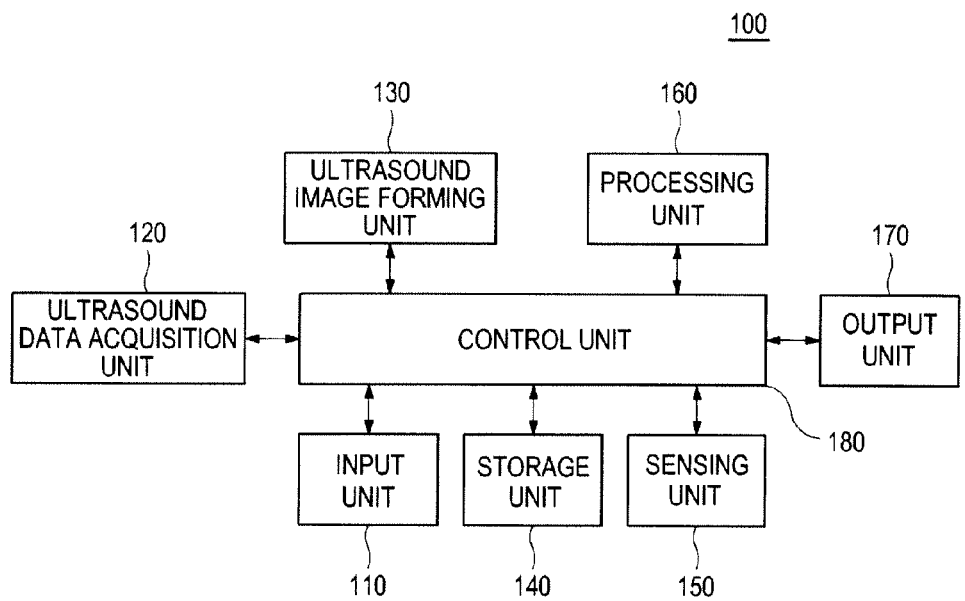
FIG. 1 is a block diagram showing an illustrative embodiment of an ultrasound system.

FIG. 1 is a block diagram showing an illustrative embodiment of an ultrasound system. As shown therein, the ultrasound system 100 may include an input unit 110 for allowing a user to input instructions. The instructions may include selection instructions for selecting a target object for diagnosis among a plurality of objects and a specific examination location for the selected target object. The instructions may further include output instructions for requesting an output of the ultrasound image and showing/hiding image indicators on a screen. The target object, examination location and image indicators will be described in detail later. The input unit 110 may include at least one of a control panel, a mouse, a keyboard, a trackball, a touch screen, etc.

Figure 2:
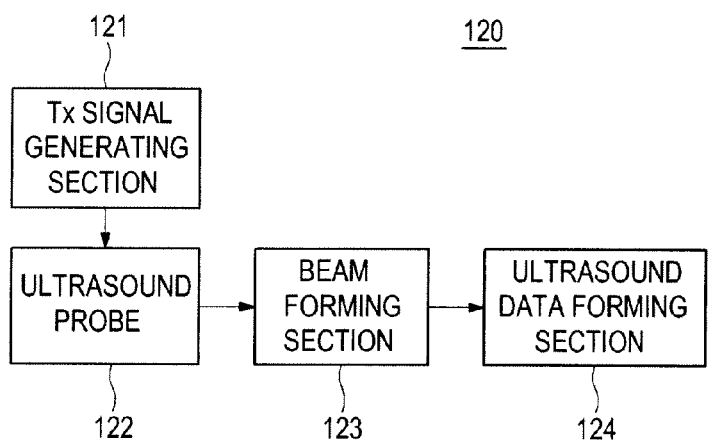
FIG. 2 is a block diagram showing an illustrative embodiment of an ultrasound data acquisition unit.

The ultrasound system 100 may further include an ultrasound data acquisition unit 120. The ultrasound data acquisition unit 120 may transmit and receive ultrasound signals to and from the target object to thereby acquire ultrasound data corresponding to a plurality of frames. Referring to FIG. 2, the ultrasound data acquisition unit 120 may include a transmit (Tx) signal generating section 121, which may be configured to generate a plurality of Tx signals.

The ultrasound data acquisition unit 120 may further include an ultrasound probe 122 coupled to the Tx signal generating section 121. The ultrasound probe 122 may transmit the ultrasound signals to the target object in response to the Tx signals. The ultrasound probe 122 may be further configured to receive echo signals reflected from the target object to thereby form electrical receive signals. The ultrasound probe 122 may contain an array transducer consisting of a plurality of transducer elements. In one embodiment, the ultrasound probe 122 may include a convex probe, a linear probe, a 3-dimensional probe, an insertion probe etc., although it is not limited thereto. The insertion probe may include a transvaginal probe and a transrectal probe.

The ultrasound data acquisition unit 120 may further include a beam forming section 123. The beam forming section 123 may apply delays to the electrical receive signals in consideration of positions of the transducer elements and focal points. The beam forming section 123 may further sum the delayed receive signals to thereby output a plurality of receive-focused beams. The ultrasound data acquisition unit 120 may further include an ultrasound data forming section 124, which may form the ultrasound data corresponding to the plurality of frames based on the receive-focused beams. The ultrasound data forming section 124 may be operable to perform signal processing upon the receive-focused beams such as gain adjustment, filtering and the like.

The ultrasound system 100 may further include an ultrasound image forming unit 130 connected to the ultrasound data acquisition unit 120 to receive the ultrasound data. The ultrasound image forming unit 130 may form an ultrasound image of the target object by using the ultrasound data. The ultrasound image may include a brightness-mode image formed by using reflection coefficients of echo signals reflected from the target object, a Doppler-mode image showing spectral Doppler representative of velocities of a moving object by using the Doppler Effect, a color-mode image showing velocities of moving objects by using predetermined colors mapped to the respective velocities, an elastic image visualizing mechanical characteristics of tissues based on strain representing deformation of tissues due to the application of the compression and the like.

Figure 4:
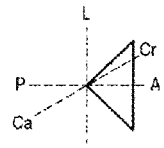
FIG. 4 is an exemplary diagram showing a mapping table associating a plurality of objects and examination locations for each of the objects with image indicators.
Figure 4:
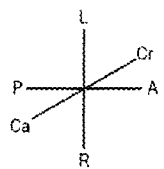
Figure 4:
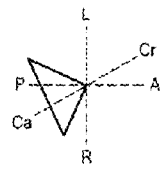
Figure 4:
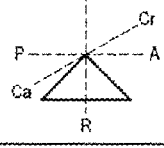
Figure 4:
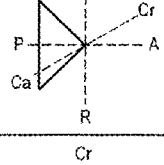
Figure 4:
Figure 4:
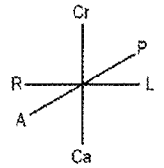
Figure 4:
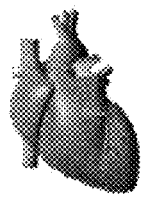
Figure 4:
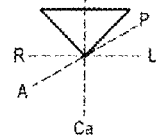

The ultrasound system 100 may further include a storage unit 140, which may store predetermined image indicators corresponding to a plurality of objects and examination locations for each object. In one embodiment, the image indicators may include target organ markers indicative of the objects such as a heart, liver, stomach, uterus, anus and the like. It may also include body axis markers indicative of anatomical orientation of the examination location for each object such as cranial Cr, caudal Ca, anterior A, posterior P, right R and left L on a 2-dimensional or 3-dimensional coordinate system. The image indicators may further include an ultrasound beam direction marker indicative of a transmission direction of an ultrasound beam transmitted from the ultrasound probe 122 for each examination location. In one embodiment, the storage unit 140 may store a mapping table associating the objects and examination locations for each object with the image indicators including the target organ markers, body axis markers and ultrasound beam direction markers, as shown in FIG. 4.

In one embodiment, the target organ markers may be 3-dimensionally or 2-dimensionally represented. Also, the body axis markers may be represented on a 3-dimensional Cartesian coordinate system. Further, the ultrasound beam direction marker may be 2-dimensionally or 3-dimensionally represented according to the type of the ultrasound probe 122. For example, when the ultrasound probe 122 is a 1-dimensional array probe, the ultrasound beam direction marker may be 2-dimensionally represented. Also, when the ultrasound probe 122 is a 2-dimensional array probe or a 3-dimensional mechanical probe, the ultrasound beam direction marker may be 3-dimensionally represented.

The ultrasound system 100 may further include a sensing unit 150, which may sense a position and/or an orientation of the ultrasound probe 122 to thereby form 3-dimensional position information and/or location information of the ultrasound probe 122. The sensing unit 150 may be mounted on a predetermined position of the ultrasound probe 122. Thus, when the ultrasound probe 122 is located in a specific examination location, the sensing unit 150 may sense the 3-dimensional position and/or orientation of the ultrasound probe 122 to form the position information and/or the orientation information. Any type of sensors capable of sensing a 3-dimensional position and/or orientation of the ultrasound probe 122 may be employed as the sensing unit 150. For example, the sensing unit 150 may include at least one of an angular velocity sensor, magnetic sensor, accelerometer sensor, gravity sensor, Gyro sensor and the like.

The ultrasound system 100 may further include a processing unit 160. The processing unit 160 may access the storage unit 140 to provide the image indicators corresponding to an object and an examination location selected in response to the instruction inputted by the user. The processing unit 160 may further 3-dimensionally rotate the provided image indicators based on the position information and/or the orientation information of the ultrasound probe 122, which is formed by the sensing unit 150.

Figure 3:
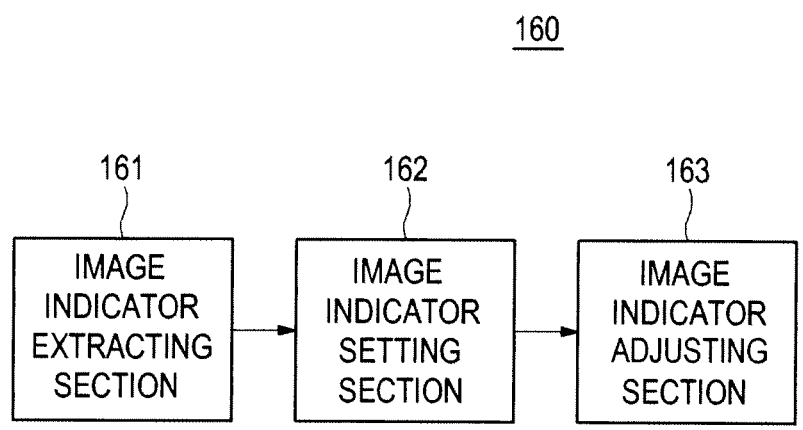
FIG. 3 is a block diagram showing an illustrative embodiment of a processing unit.

FIG. 3 is a block diagram showing an illustrative embodiment of the processing unit 160. Referring to FIG. 3, the processing unit 160 may include an image indicator extracting section 161. The image indicator extracting section 161 may access the storage unit 140 in response to the selection instruction inputted by the user to extract the image indicators (i.e., target organ marker, body axis marker and ultrasound beam direction marker). For example, if the selection instructions for selecting the uterus as a target object and the vagina as an examination location are inputted through the input unit 110, then the image indicator extracting section 161 may access the storage unit 140 to extract the corresponding image indicators including the target organ marker, body axis marker and ultrasound beam from the mapping table. Also, the selection instructions for selecting the heart as the target object and the parasternal view as the examination location are inputted through the input unit 110, the image indicator extracting section 161 may access the storage unit 140 to extract the image indicators including the target organ marker, body axis marker and ultrasound beam corresponding to the heart and the parasternal view.

Figure 5:
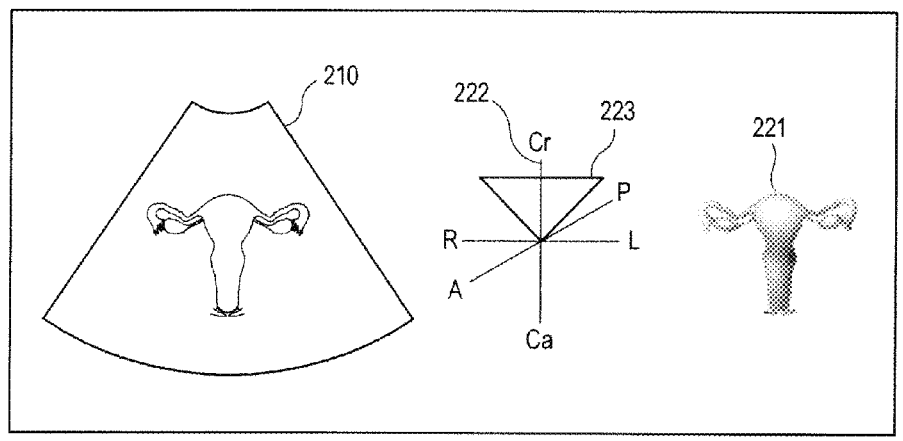
FIG. 5 is a schematic diagram showing an example of displaying image indictors together with an ultrasound image.

The processing unit 160 may further include an image indicator setting section 162. The image indicator setting section 160 may perform orientation setting of the extracted image indicators based on the position information of the ultrasound probe 122. The image indicators, which are set by the image indicator setting section 160, may be outputted to an output unit 170. The output unit 170 may include a display unit (not shown) such as a CRT monitor, LCD display, OLED display and the like to display the ultrasound image. Further, the output unit 170 may include an echo printer (not shown) to print out the ultrasound image and the image indicators. For example, the image indicator setting section 162 may arrange the extracted body axis marker 222 and ultrasound beam direction marker 223 based on anatomical characteristics of the target object, and set the ultrasound beam direction marker 223 to be overlaid over the body axis marker 222, as shown in FIG. 5. Further, the image indicator setting section 162 may position the target organ marker 221 at the right side of the body axis marker 222 and the ultrasound beam direction marker 223 to perform the orientation setting upon the body axis marker 222, the ultrasound beam direction marker 223 and the target organ marker 221 based on the position information and/or the orientation information.

Although the above embodiment has been described that the body axis marker is overlaid over the ultrasound beam marker and the target organ marker is positioned at the right side of the body axis marker, the arrangement thereof may not be limited thereto. The body axis marker, the ultrasound beam direction marker and the target organ marker may be set to be overlaid or to be separated from each other.

Figure 6:
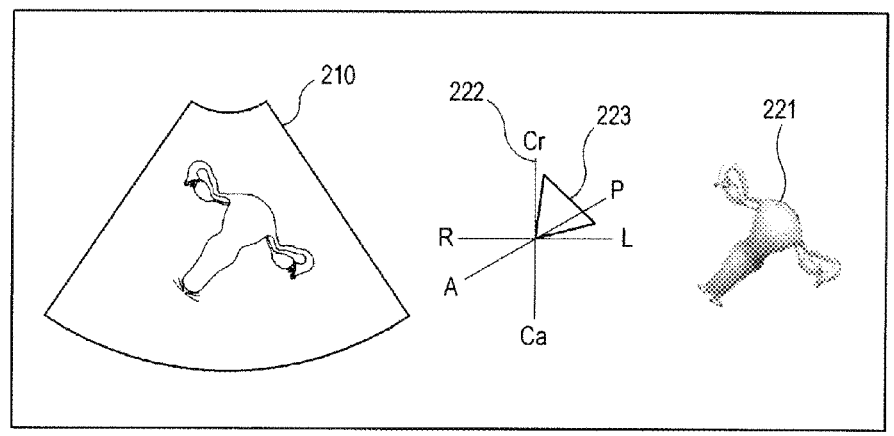
FIG. 6 is a schematic diagram showing an example of displaying image indicators together with an ultrasound image, wherein their orientation has been adjusted according to position information of an ultrasound probe.

The image processing unit 160 may further include an image indicator adjusting section 163. If the ultrasound probe 122 is moved along a predetermined guide line, then the position information and/or the orientation information of the ultrasound probe 122 may be changed. The image indicator adjusting section 163 may be configured to adjust the image indicators based on the changed position information and/or orientation information. For example, the image indicator adjusting section 163 may rotate the image indicators 3-dimensionally based on the changed position information and/or orientation information. The image indicator adjusting section 163 may compute a position difference or an orientation difference of the ultrasound probe 122 based on the changed position information, and 3-dimensionally rotate the image indicators including the target organ marker 221, the body axis marker 22 and the ultrasound beam direction marker 223 based on the computed position difference and/or orientation difference, as illustrated in FIG. 6. In FIGS. 5 and 6, reference numeral "210" may represent an ultrasound image. The image indicator adjusting section 163 may further show or hide the image indicator in response to a instruction for showing/hiding the image indicators on a screen, which may be inputted through the input unit 110.

Referring back to FIG. 1, the ultrasound system 100 may further include a control unit 180. The control unit 180 may control the transmission and reception of the ultrasound signals in the ultrasound data acquisition unit 120 according to an image mode. Further, the control unit 180 may be configured to control entire operations of the elements of the ultrasound system 100.

While the present invention is described by some preferred embodiments, it will be appreciated by those skilled in the art that many modifications and changes can be made without departing from the spirit and scope of the appended claims.

What is claimed is:

1. An ultrasound system, comprising:
a sensing unit configured to sense a 3-dimensional position and/or orientation of an ultrasound probe to form position information and/or orientation information;
a display; and
a processor configured to control the display to display one or more image indicators including an ultrasound beam direction marker depicting a direction of an ultrasound beam transmission transmitted from the ultrasound probe, and a target organ marker depicting a target object in a body, the ultrasound beam direction marker and the target organ marker being overlaid on each other,
wherein the processor is further configured to 3-dimensionally rotate the ultrasound beam direction marker based on the position information and/or the orientation information of the ultrasound probe and to control the display to display a body axis marker in a 3-dimensional coordinate system indicating an anatomical orientation of the displayed target organ with respect to the body, and
the body axis marker is displayed differently depending on the anatomical orientation of the displayed target organ in the 3-dimensional coordinate system.

2. The ultrasound system of claim 1, wherein the body axis marker is differently displayed based on the anatomical orientation determined according to examination locations.

3. The ultrasound system of claim 2, further comprising:
a storage unit configured to store a mapping table including a plurality of objects each associated with examination locations, each of the examination locations being associated with the one or more image indicators; and
an input unit configured to allow a user to input a selection instruction for selecting the target object among the plurality of objects and one of the examination locations for the target object,
wherein the processor is configured to access the storage unit to provide the one or more image indicators corresponding to the target object and the one of the examination locations in response to the selection instruction.

4. The ultrasound system of claim 3, wherein the ultrasound beam direction marker is 2-dimensionally or 3-dimensionally represented according to a type of the ultrasound probe.

5. The ultrasound system of claim 3, wherein the sensing unit is selected from the group consisting of an angular velocity sensor, magnetic sensor, accelerometer sensor, gravity sensor, Gyro sensor and combinations thereof.

6. The ultrasound system of claim 3, wherein the processor includes:
an image indicator extracting section configured to access the storage unit to extract the target organ marker, the body axis marker and the ultrasound beam direction marker corresponding to the target object and the examination location selected in response to the instruction;
an image indicator setting section configured to perform orientation setting upon the extracted target organ marker, body axis marker and ultrasound beam direction marker based on the position information and/or the orientation information; and
an image indicator adjusting section configured to rotate the extracted target organ marker, body axis marker and ultrasound beam direction marker 3-dimensionally based on position information and/or orientation information changed due to a movement of the ultrasound probe.

7. The ultrasound system of claim 6, wherein the image indicator setting section is configured to arrange the extracted target organ marker, and the body axis marker based on anatomical characteristics of the target object.

8. The ultrasound system of claim 3, wherein the input unit is configured to allow the user to input instructions for showing/hiding at least one of the image indicators.

9. The ultrasound system of claim 8, wherein the processor is configured to show/hide the at least one of the image indicators in response to the instructions for showing/hiding the at least one of the image indicators.

10. The ultrasound system of claim 3, further comprising an output unit to output at least one of the image indicators.

11. A method of providing an image indicator in an ultrasound system including an ultrasound probe, the method comprising:
a) sensing a position and/or an orientation of the ultrasound probe by using a sensing unit to form position information and/or orientation information;
b) displaying one or more image indicators including an ultrasound beam direction marker depicting a direction of an ultrasound beam transmission transmitted from the ultrasound probe, and a target organ marker depicting a target object in a body, the ultrasound beam direction marker and the target organ marker being overlaid on each other;
c) displaying a body axis marker in a 3-dimensional coordinate system indicating an anatomical orientation of the displayed target organ with respect to the body; and (d) 3-dimensionally rotating the ultrasound beam direction marker based on the position information and/or the orientation information, wherein the body axis marker is displayed differently depending on the anatomical orientation of the displayed target organ in the 3-dimensional coordinate system.

12. The method of claim 11, wherein the body axis marker is differently displayed based on the anatomical orientation determined according to examination locations.

13. The method of claim 12, further comprising:
(e) storing a mapping table including a plurality of objects each associated with the examination locations, each of the examination locations being associated with the one or more image indicators;
(f) inputting one or more selection instructions for selecting the target object among the plurality of objects and one of the examination locations for the target object; and
(g) accessing a storage unit to provide image indicators corresponding to the selected target object and the selected examination location in response to the inputted instructions.

14. The method of claim 13, wherein the ultrasound beam direction marker is 2-dimensionally or 3-dimensionally represented according to a type of the ultrasound probe.

15. The method of claim 13, wherein the sensing unit is selected from the group consisting of an angular velocity sensor, magnetic sensor, accelerometer sensor, gravity sensor, Gyro sensor and combinations thereof.

16. The method of claim 13, wherein step d) includes:
accessing the storage unit to extract the target organ marker, the body axis marker and the ultrasound beam direction marker corresponding to the target object and the examination location selected in response to the instructions; and
performing orientation setting upon the extracted target organ marker, body axis marker and ultrasound beam direction marker based on the position information and/or the orientation information.

17. The method of claim 16, wherein step d) includes 3-dimensionally rotating at least one from among the extracted target organ marker, the body axis marker and the ultrasound beam direction marker based on position information and/or orientation information changed due to a movement of the ultrasound probe.

18. The method of claim 17, wherein step d) further includes arranging the extracted target organ marker, and the body axis marker based on anatomical characteristics of the target object.

19. The method of claim 13, further comprising inputting instructions for showing/hiding at least one of the image indicators.

20. The method of claim 19, further comprising showing/hiding at least one of the image indicator in response to the instructions for showing/hiding the at least one of the image indicators.

21. The method of claim 13, further comprising outputting at least one of the image indicators.

* * * * *